United States Patent [19]
Lubbe

[11] Patent Number: 5,628,768
[45] Date of Patent: May 13, 1997

[54] NERVE STIMULATOR WITH EXPONENTIAL DECAY OUTPUT FEATURE

[75] Inventor: Anton Lubbe, Pretoria, South Africa

[73] Assignee: Tech Pulse (Proprietary) Limited, Pretoria, South Africa

[21] Appl. No.: 314,159

[22] Filed: Sep. 28, 1994

[30] Foreign Application Priority Data

Sep. 29, 1993 [ZA] South Africa .............. 93/7235

[51] Int. Cl.⁶ .................. A61N 1/32; A61N 1/36
[52] U.S. Cl. .................. 607/46; 607/63; 607/74
[58] Field of Search .................. 607/46, 59, 62, 607/63, 74, 64, 68

[56] References Cited

U.S. PATENT DOCUMENTS

| | | | |
|---|---|---|---|
| 3,160,159 | 12/1964 | Hoody et al. | 607/68 |
| 3,810,457 | 5/1974 | Bottcher | 128/2.1 |
| 3,989,051 | 11/1976 | Nozhnikov | 128/421 |
| 4,102,347 | 7/1978 | Yukl | 128/421 |
| 4,340,063 | 7/1982 | Maurer | 128/421 |
| 4,372,319 | 2/1983 | Ichinomiya | 128/421 |
| 4,459,988 | 7/1984 | Dugot | 128/419 |
| 4,528,984 | 7/1985 | Morawetz | 128/421 |
| 4,539,993 | 9/1985 | Stonton | 128/421 |
| 4,622,973 | 11/1986 | Agarwala | 128/421 |
| 4,769,881 | 9/1988 | Pedigo et al. | 607/63 |
| 5,067,475 | 11/1991 | Brehm | 607/46 |
| 5,117,826 | 6/1992 | Bartelt et al. | 607/46 |
| 5,146,920 | 9/1992 | Yuuchi et al. | 607/63 |
| 5,184,617 | 2/1993 | Harris | 128/423 |
| 5,222,494 | 6/1993 | Baker | 128/421 |
| 5,273,033 | 12/1993 | Hoffman | 607/46 |
| 5,342,410 | 8/1994 | Braverman | 607/46 |
| 5,431,625 | 7/1995 | Fabian et al. | 607/63 |
| 5,514,165 | 5/1996 | Malaugh et al. | 607/46 |
| 5,540,734 | 7/1996 | Zabara | 607/46 |

FOREIGN PATENT DOCUMENTS

| | | | |
|---|---|---|---|
| 0290126 | 3/1987 | European Pat. Off. | A61N 1/32 |
| 0335266 | 3/1989 | European Pat. Off. | A61N 1/08 |
| 0339313 | 4/1989 | European Pat. Off. | A61N 1/08 |
| 2502015 | 3/1981 | France | A61N 1/32 |
| 2684872 | 12/1991 | France | A61N 1/32 |
| 2507783 | 2/1975 | Germany | A61N 1/32 |
| 2085733 | 10/1980 | United Kingdom | A61N 1/08 |
| 2052991 | 2/1981 | United Kingdom | A61N 1/08 |
| 2099705 | 6/1981 | United Kingdom | A61N 1/32 |
| 2123698 | 6/1982 | United Kingdom | A61N 1/08 |
| 9422529 | 10/1994 | WIPO | 607/46 |

*Primary Examiner*—William E. Kamm
*Assistant Examiner*—Carl H. Layno
*Attorney, Agent, or Firm*—Ladas & Parry

[57] ABSTRACT

A nerve stimulation apparatus includes a waveform generator capable of generating a waveform comprising a sequence of pulses, and a controller. The pulses 20 have parameters as follows, a repetition rate of 150 to 200 Hz, a pulse width of 0,8 to 1,2 ms, a pulse decay which is exponential, an amplitude of between 40 to 60 volts with a negative DC off-set, and an output current of 0,01 to 10 mA. The controller controllably varies the parameters of the pulse generator. A method of controlling pain in a human subject includes applying the waveform to the human subject.

7 Claims, 6 Drawing Sheets

NERVE STIMULATOR WITH EXPONENTIAL DECAY OUTPUT FEATURE

FIELD OF THE INVENTION

This invention relates to a nerve stimulation apparatus and method. It relates in particular to a nerve stimulation apparatus and a method of controlling pain in a human subject.

DESCRIPTION OF THE PRIOR ART

In the prior art, electrical nerve simulators are known which suppress organic pain by applying pulses through the skin to stimulate the peripheral nerve fibres, mainly sensory nerve fibres, while objectionable sensations are eliminated by varying the pulse amplitude, pulse duration and/or pulse repetition rate, thereby placing very restrictive parameters on the operation of such devices. However this treatment does not eliminate the adaptation phenomenon of receptors and nerve cells to sensory impulses.

Further, the prior art devices mainly concentrate on stimulating sensory nerve fibres, which results in a blockage of pain impulses. They all attempt to cope with the adaptation problem, whereby optimum muscle fasciculation is not achieved, resulting in incomplete tetanus, then complete tetanus, and then muscle fatigue.

SUMMARY OF THE INVENTION

An object of this invention is to provide an apparatus for, and a method of, stimulation in which optimum muscle fasciculation. Use of the apparatus is facilitated as no adjustments, manually or via software are necessary during the treatment.

According to the invention there is provided a nerve stimulation apparatus which includes a waveform generator capable of generating a waveform comprising a sequence of pulses having parameters as follows, a repetition rate of 150 to 200 Hz, a pulse width of 0,8 to 1,2 ms, a pulse decay which is exponential, an amplitude of between 40 to 60 volts with a negative DC off-set, and an output current of 0,01 to 10 mA; and a controller connected to the waveform generator for controllably varying at least one of the parameters.

The apparatus may include a pulse signal circuit for generating a pulsed input signal. The waveform generator may then include current regulating means responsive to the pulsed input signal and operable to regulate an output of the waveform generator in sympathy with the pulsed input signal; and a voltage source connectable by a series connection with the current regulating means, the series connection being provided by a load connected to output terminals of the apparatus in use.

The voltage source may have voltage off-set means operable to adjust the negative DC off-set of the waveform so that each pulse has a positive peak of 10 to 600 mV.

The controller may include signal generating means for generating a current control signal, the current regulating means being responsive to the current control signal thereby to vary the output current from the waveform generator.

The voltage source may include a switching circuit which comprises a high frequency oscillator for generating a high frequency output signal;

a coil connected to an output of the high frequency oscillator and to which the high frequency output signal is applied in use; and rectifier means connected to the coil and arranged to rectify the high frequency output signal to provide a rectified output voltage at an output of the voltage source.

The voltage source may further include a feedback circuit operable to increase the frequency of the high frequency oscillator upon a decrease in an RMS value of the rectified output voltage of the voltage source thereby to maintain a constant rectified output voltage at the output of the voltage source.

The controller may include a microprocessor having software for controlling the waveform generator. The controller may also include a frequency to voltage converter connected to the microprocessor and operable to convert a frequency dependent signal, which is sourced from the microprocessor and representative of a desired output current, to a voltage dependent signal which is fed into the waveform generator thereby to control the output current of the waveform generator. The controller may include frequency selection means whereby the repetition rate of the waveform may be selected. The frequency selection means may be by means of links or switches hardwired to the controller. The frequency selection means may also operate in conjunction with software programmed into the controller.

The controller may include timing means operable to interrupt application of the waveform after a preselected time period. The timing means may have selection means for selecting the time period. When the controller is a microprocessor based controller the timing means may be implemented by software programmed into the controller.

The apparatus may include input means, e.g. in the form of a keypad connected to the controller, for inputting data into the controller, e.g. to select the time period provided by the timing means, a desired current level, and so on.

The apparatus may include display means for displaying magnitude of the output current of the waveform. During operation, the timing means may also be arranged to display the duration of operation of the apparatus via the display means.

The invention extends also to a method of controlling pain in a human subject, which includes generating a waveform comprising a sequence of pulses having parameters as follows, a repetition rate of 150 to 200 Hz, a pulse width of 0,8 to 1,2 ms, a pulse decay which is exponential, an amplitude of between 40 and 60 volts with a negative DC off-set, and an output current of 0,01 to 10 mA; and applying the waveform to the human subject.

BRIEF DESCRIPTION OF THE DRAWINGS

An embodiment of the invention is now described, by way of example, with reference to the accompanying diagrammatic drawings.

DESCRIPTION OF THE PREFERRED EMBODIMENT

Figure 1:
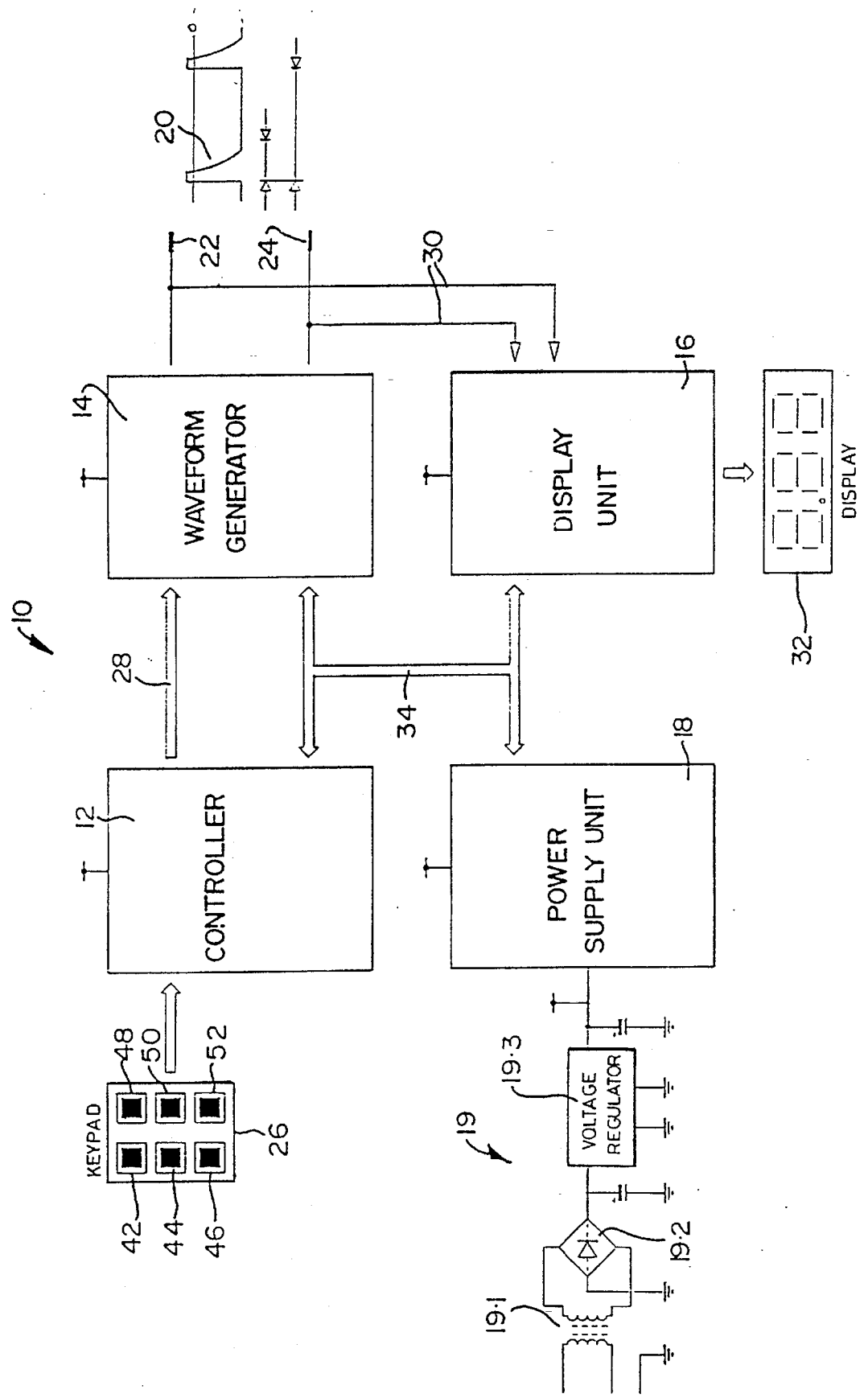
Figure 2:
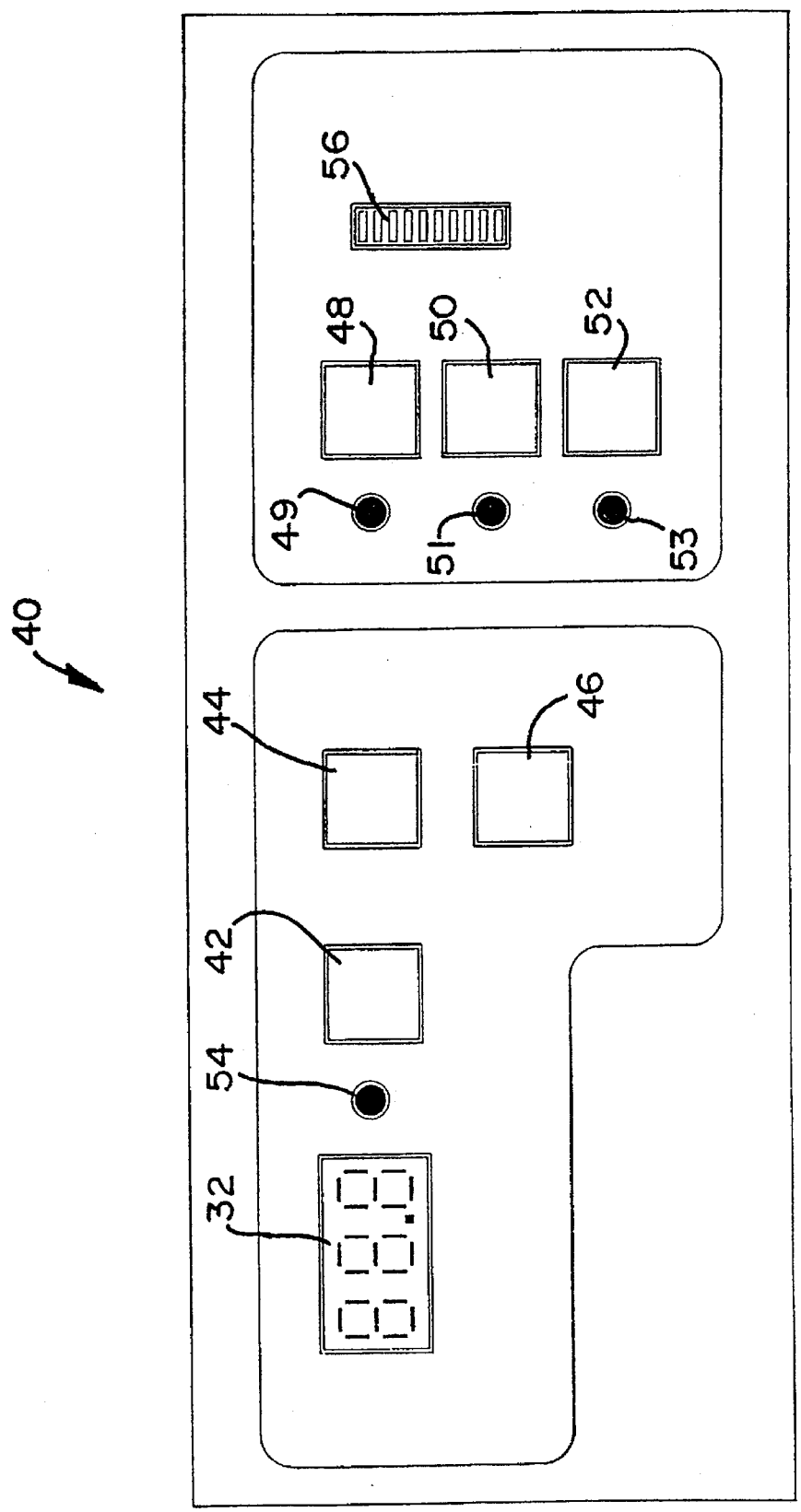
Figure 3:
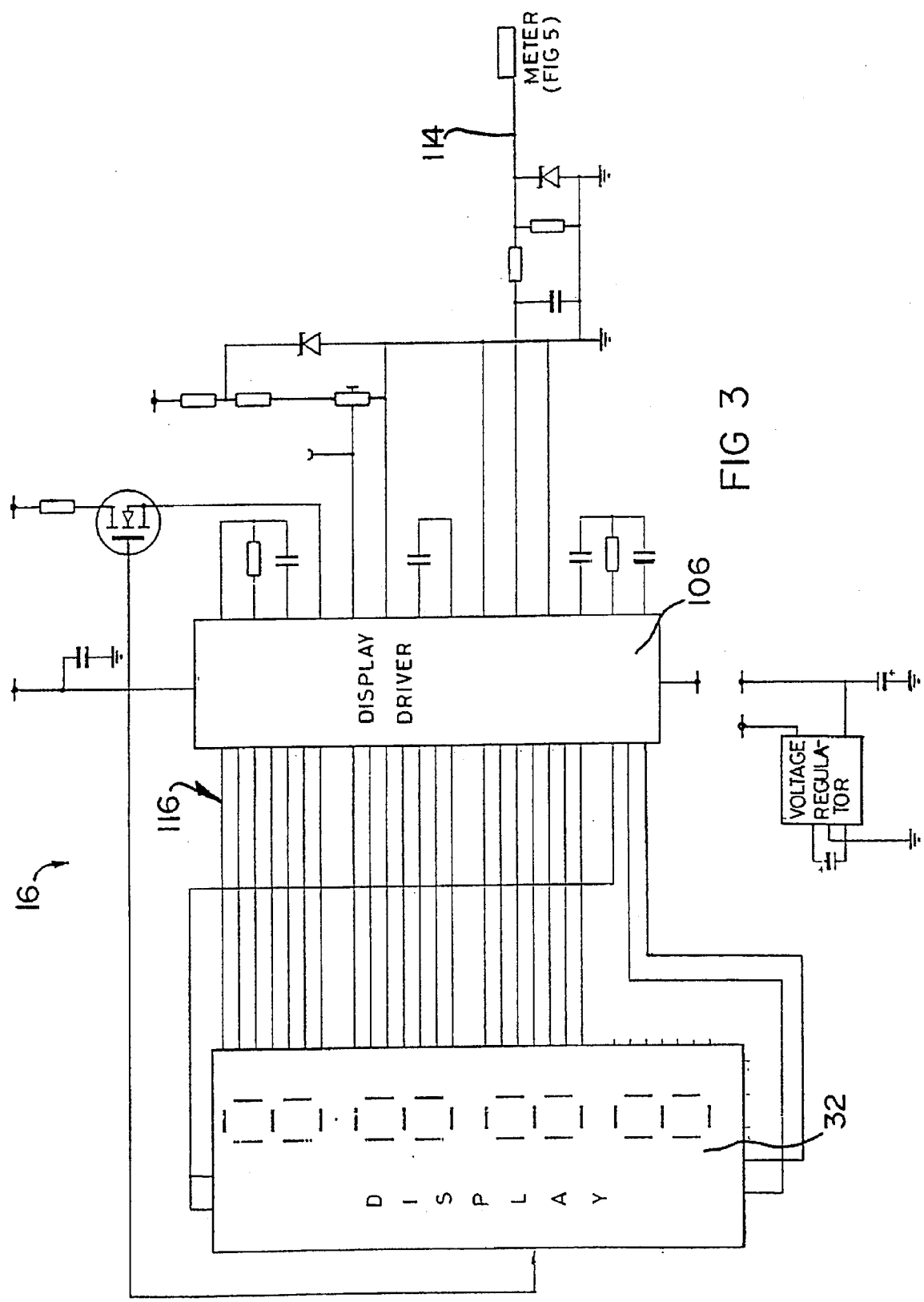
Figure 4:
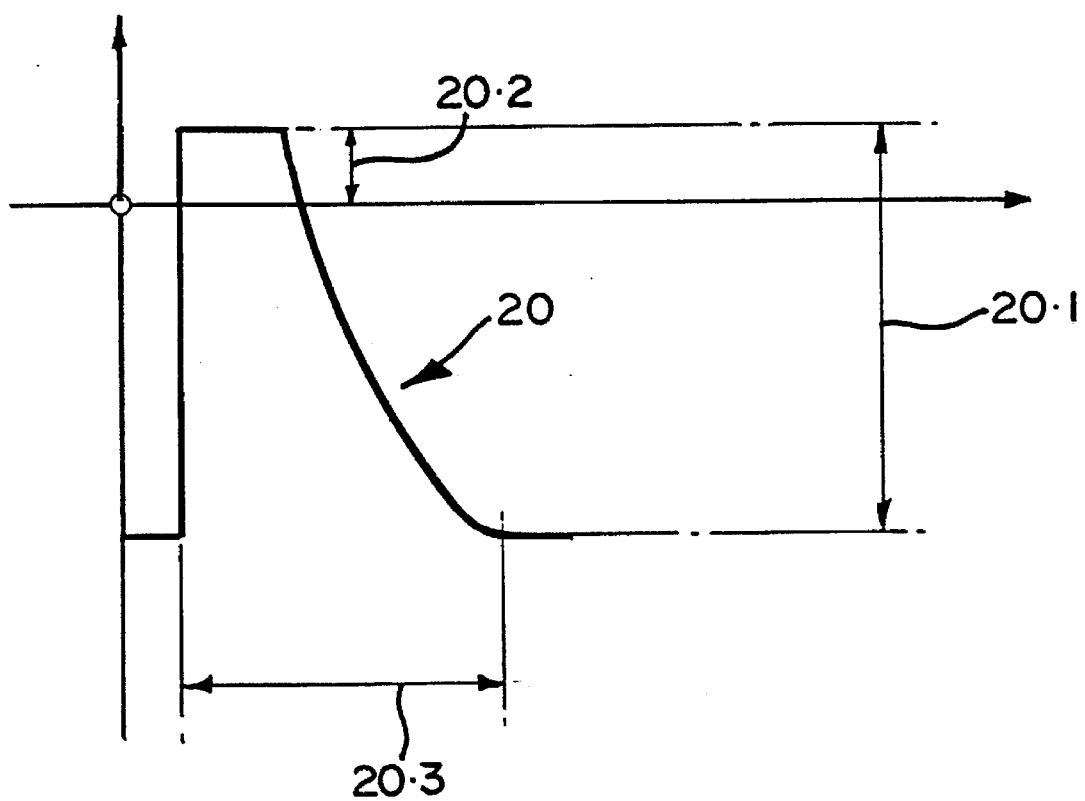
Figure 5:
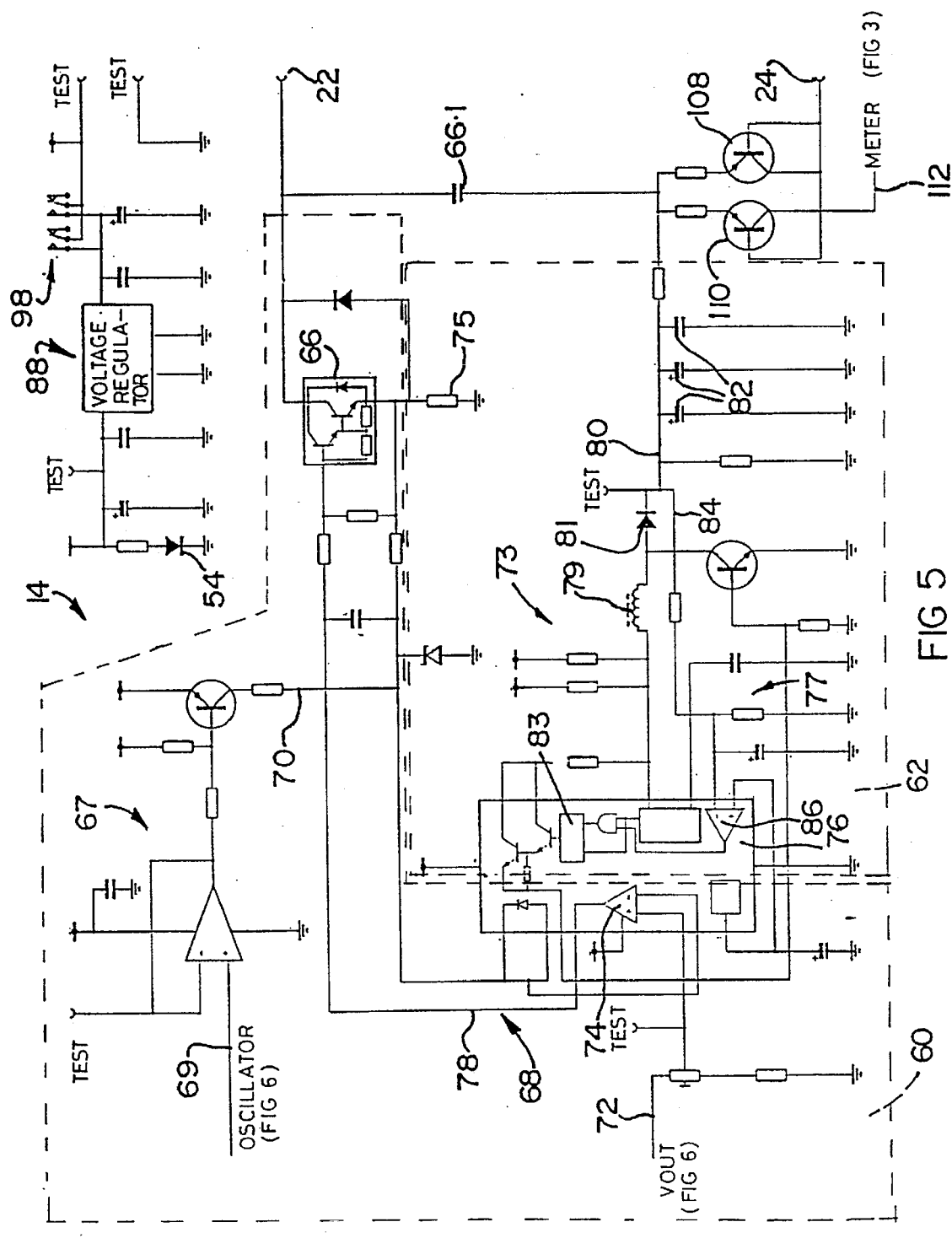
Figure 6:
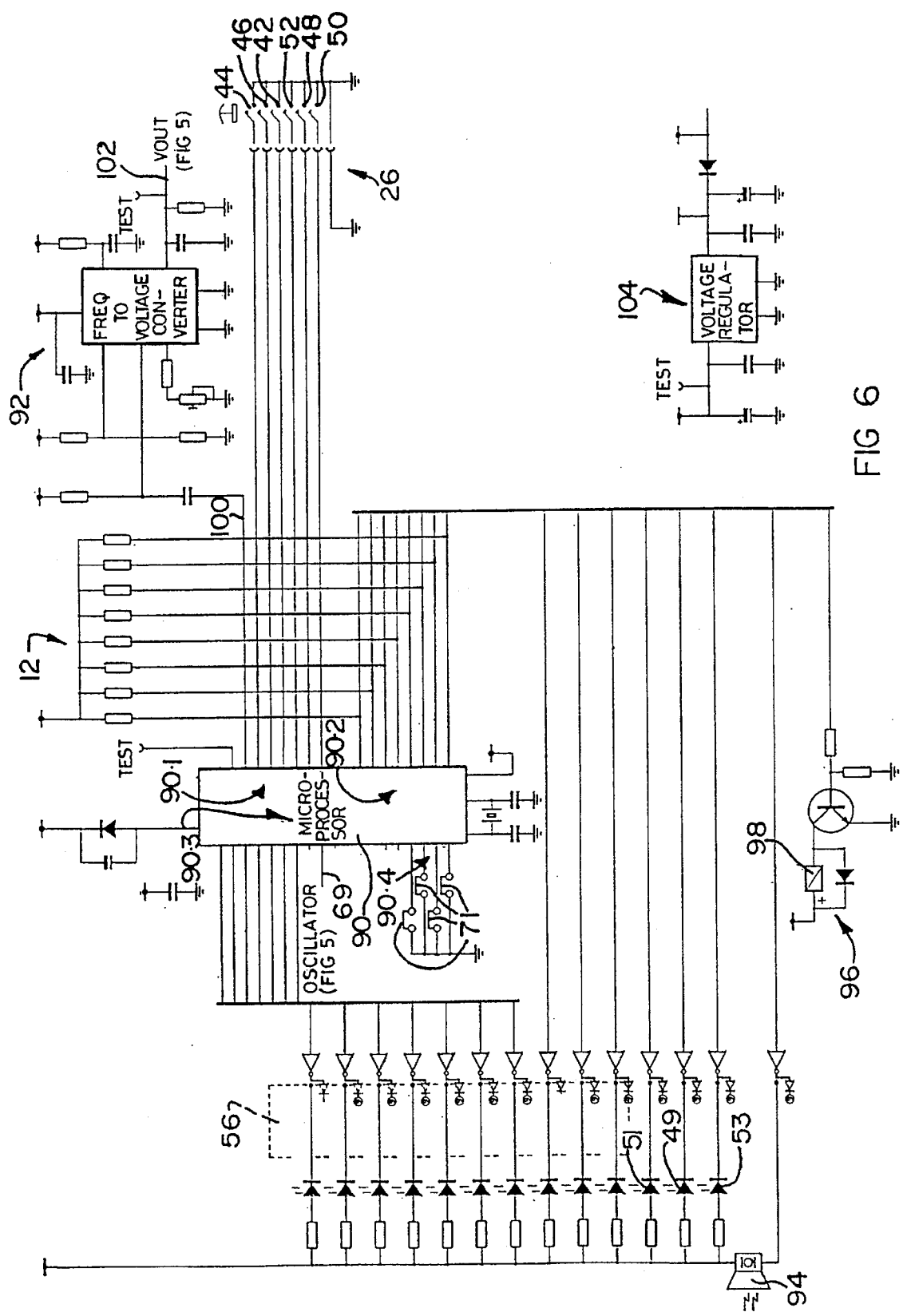

In the drawings,

FIG. 1 shows a schematic block diagram of a nerve stimulation apparatus in accordance with the invention;

FIG. 2 shows a front elevation of a control panel of the apparatus of FIG. 1;

FIG. 3 shows a schematic circuit diagram of a display unit used in the apparatus of FIG. 1;

FIG. 4 shows a time domain representation of the waveform generated by the apparatus of FIG. 1 (which is not to scale);

FIG. 5 shows a schematic circuit diagram of a waveform generator used in the apparatus of FIG. 1; and FIG. 6 shows a schematic circuit diagram of a microprocessor based controller used to control the waveform generator of FIG. 5.

Referring to FIG. 1, reference numeral 10 generally indicates a nerve stimulation apparatus primarily intended for use in a method of treatment of and controlling pain in a human subject. The apparatus 10 includes a microprocessor based controller 12, a waveform generator 14, a display unit 16, and a power supply unit 18.

The waveform generator 14 generates a sequence of generally square pulses 20, the preferred form of which is shown in FIG. 4. The waveform has been selected to simulate the so-called human nerve action potential which it is believed is a naturally occurring nerve impulse substantially similar to that shown in FIG. 4. The pulses 20 are emitted from output terminals 22, 24 of the waveform generator 14.

Generally, as shown in FIG. 4, each pulse 20 has an amplitude 20.1 of about 40 volts to about 60 volts, preferably about 46 volts, with a negative DC off-set so that each pulse commences from a negative level of close to about −40 volts to −60 volts. A leading edge of the pulse rises steeply. Each pulse 20 has a positive peak 20.2 of about +10 mV to about +600 mV, preferably about 500 mV, and has a pulse width 20.3 of about 0.8 ms to about 1.2 ms, preferably about 1 ms. The repetition rate of the pulses 20 is between 150 Hz and 200 Hz, preferably about 150 Hz. The pulses 20 have a constant current output which is adjustably variable between 0.01 mA and about 10 mA. After remaining at its peak at a substantially constant amplitude for about 0.2 ms, the pulse decays exponentially as shown. The duration of the exponential decay is up to about 1 ms.

The controller 12 controls the waveform generator 14 via a control bus 28 and system parameters are fed by an operator into the controller 12 via a keypad 26, the controller 12 thereby controlling the output parameters of the pulse 20. The output current is determined by the controller 12 which in turn controls the waveform generator 14 via the bus 28. The selected system parameters are then displayed by the display unit 16, as described below.

The output terminals 22, 24 of the waveform generator 14 are connected to electrode pads (not shown) which are operatively applied to the skin of a person and which are preferably in the form of plasma covered metal foil. An output current fed to the electrodes is also fed via lines 30 into the display unit 16 which has a liquid crystal display 32 for displaying the amplitude of the output current.

The power supply unit 18 is fed with a 9 V regulated power signal via a supplementary power supply 19. The supplementary power supply 19 has a step down transformer 19.1 which has a primary winding connected to a mains line and a secondary winding connected to a rectifier 19.2. An output of the rectifier 19.2 is fed via a 9 V voltage regulator 19.3 into the power supply unit 18.

The power supply unit 18 provides power to the display unit 16, the waveform pulse generator 14, and the controller 12 via a power supply bus 34. The bus 34 is a bi-directional bus thereby to enable the controller 12 to switch itself off after a preselected time period has lapsed. The time period is selected by entering via the keypad 26.

Referring to FIG. 2, reference numeral 40 generally indicates a control panel on which various membrane switches 42 to 52 of the keypad 26 are mounted. The switch 42 is an on/off switch for switching the apparatus 10 on and off and an LED 54 is illuminated when the apparatus 10 is switched on.

In use, the controller 12 is responsive to the switches 44 and 46 which, respectively, increase and decrease the output current upon actuation. The display 32 displays the output current from the waveform generator 14 thereby enabling an operator to monitor the current magnitude in use.

The switches 48 and 50 are used to select duration of operation of the apparatus 10. Switch 48 is a ten minute time period selector which, upon actuation, illuminates an LED 49 and provides a ten minute input signal to the controller 12. Likewise, upon actuation of the switch 50 a five minute timing signal is provided to the controller 12 and an LED 51 is illuminated. The switch 52 is a start/reset switch which, upon actuation, illuminates an LED 53 and provides a start/reset signal to the controller 12. A bar graph display 56, formed by a plurality of stacked LED's, indicates the progression of the selected time by displaying the time remaining of the initial time period selected.

The waveform generator 14 has current regulating circuitry 60 (FIG. 5) which regulates the output current of the waveform generator 14, and a voltage source 62 which is operatively connected in series with the current regulating circuitry 60. The series connection between the current regulating circuitry 60 and the voltage source 62 is provided in use by a patient's body.

The current regulating circuitry 60 includes a driver circuit 67, a Darlington transistor configuration 66 and current adjustment circuitry 68. A pulsed input signal is fed into the driver circuit 67 via a line 69 from the controller 12. The pulsed input signal is then fed into the transistor configuration 66 via a line 70 thereby regulating the output waveform in sympathy with a level of the pulsed input signal.

The degree of negative off-set and the amplitude of the positive peak 20.2 relative to zero volts of the waveform shown in FIG. 4 and emitted from the output terminals 22, 24 is consequent upon the current flowing in an emitter resistor 75 and the saturation voltage of the transistor configuration 66 which provides the negative off-set to the waveform. The degree of off-set and the level of the positive peak 20.2 varies depending upon the amount of current drawn by the load. The exponential decay of the pulse is provided by a capacitor 66.1 so that each pulse is fully discharged into the patient from the terminals 22, 24. It will be noted that neither of the terminals 22, 24 is earthed so that the patient's body is in a floating series configuration with the apparatus.

A current control signal from the controller 12 is fed via a line 72 to a differential amplifier 74 of the current adjustment circuitry 68. An output from the differential amplifier 74 is fed via a line 78 to the transistor configuration 66 which controls the output current on the output terminals 22, 24.

The voltage source 62 includes a high frequency oscillator 73 implemented by sub-components of an integrated circuit 76 and associated circuitry, a coil 79 to which the high frequency output signal is applied, and a rectifier 81 connected to the coil 79, which rectifies the high frequency signal providing a rectified DC output voltage on line 80. Smoothing capacitors 82 are provided to improve regulation.

The voltage source 62 includes a feedback circuit 77 which is connected intermediate the output of the voltage source 62 and the high frequency oscillator 73. The feedback circuit 77 increases the frequency of the oscillator 73 upon a decrease in the RMS value of the output voltage on line 80 thereby to maintain the RMS value of the output voltage at a constant level. The feedback circuit 77 includes a feedback path 84 to feed back the output voltage on line 80 to a differential amplifier 86. An output from the differential amplifier 86 is fed into a flip-flop 83 and switching circuitry of the integrated circuit 76.

The waveform generator 14 also has power supply circuitry 88 which provides a 6 V regulated output to its various components.

FIG. 6 shows a schematic circuit diagram of the controller 12 which controls the operation of the apparatus 10. The controller 12 comprises a microprocessor 90, typically an (OTP) 87C51 microprocessor, connected to the switches 42 to 52, a frequency to voltage converter 92, the display 56 for indicating the progression of time, a buzzer 94 and power cut-off circuitry 96. Timing means which is implemented by the microprocessor 90 and software loaded therein, disables the waveform generator 14 after a preselected time period via the bi-directional bus 34. The buzzer 94 is actuated upon the lapsing of the preselected time period thereby indicating that the time period selected has expired. The power cut-off circuitry 96 includes a relay 98 which is configured to interrupt power to the apparatus 10.

The switches 42 to 52 of the keypad 26 are connected to a first input/output port 90.1 of the microprocessor 90. Second and third input/output ports 90.2 and 90.3 are connected to and drive the display 56. The LEDs 49, 51 and 53 which respectively indicate the selection of the ten minute and five minute time period, and the start/reset condition correspond with those shown in FIG. 2.

The microprocessor 90 generates the pulsed input signal at the port 90.3 which is then fed into the driver circuit 67 (FIG. 5) via line 69. A port 90.4 is used to select a particular repetition rate of the pulsed input signal which, in turn, determines the repetition rate of the pulse 20. The controller 12 has a plurality of frequency selection means in the form of links or jumpers 71 which are connected to the port 90.4. Each particular jumper 71, when located in position, selects a predetermined frequency at which the pulse 20 is applied to the load via the output terminals 22, 24.

The microprocessor 90 provides a frequency dependent current control output signal on line 100, which is representative of a current selected by means of the current up switch 44 and the current down switch 46. A higher frequency on line 100 is representative of a higher current and a lower frequency is representative of a lower current. The current control signal on line 100 is fed into the frequency to voltage converter 92 which converts the signal to a voltage dependent signal on line 102. The voltage dependent signal on line 102 is then fed into the waveform generator 14 via line 72 (FIG. 5). The controller 12 further includes a power supply 104 to provide a regulated 5 V output to the microprocessor 90.

FIG. 3 shows a schematic circuit diagram of the display unit 16 used in the apparatus 10. The display unit 16 comprises the liquid crystal display 32, a display driver 106, typically an ICL 7106, and associated circuitry. As shown in FIG. 5, a transistor 108 is connected in series between the output terminal 24 and the voltage source 62. A second transistor 110, which has the same base current as the transistor 108, provides a signal on line 112 which is representative of the output current flowing from the apparatus 10. The signal on line 112 (FIG. 5) is fed via line 114 (FIG. 3) into the display unit 16.

The Applicant believes that the pulse 20 generated by the apparatus 10 is particularly effective in electrotherapy. When the apparatus 10 is operative and the electrodes connected to output terminals 22, 24 are secured to the skin of a patient, current flows in the body of the patient via the electrodes. The Applicant believes that the current flow with the specific parameters selected has a beneficial effect on the neurons and biochemical functions of the body of the patient by stimulating nerve fibres or axons by lowering the membrane potentials of the axons. It is believed that axons inherently have the necessary energy to produce the so-called action potential and application of the FIG. 4 waveform triggers the axons into action.

The Applicant believes that application of the pulsed waveform 20 of FIG. 4 causes depolarization of the nerve fibres in the human body provided that the strength and duration of the pulsed waveform are of sufficient magnitude. Because the pulse shown in FIG. 4 has a negative off-set relative to zero volts as shown rather than being a symmetrical pulse relative to zero volts or being a predominantly positive pulse relative to zero volts, the Applicant believes that this gives rise to a greater hypopolarizing effect on the nerve fibres and thus the pulse 20 generated by the apparatus 10 is particularly effective in electrotherapy.

It is believed that the low-frequency pulse 20 produces synchronous depolarization of the nerve fibres. Thus, after the pulse 20 is applied to the skin of the human body via the electrodes, nerve fibres, not only close to the skin but also remote from the skin, gradually become depolarized. The effect of this depolarization is a reduction in pain and it relaxes the patient and improves the blood circulation of the patient.

The Applicant further believes that stimulation of thick afferent nerve fibres in the body has an inhibiting or blocking effect on the activity of thin afferent nerve fibres, and consequently pain perception is diminished. In addition to reducing pain by stimulation of the thick nerve fibres, normalization of the neuro-vegetative balance occurs. This means a damping of the orthosympathetic system which is reflected in relaxation and improvement of the circulation of the blood. Stimulation of myelinate afferent nerve fibres in muscle or skin tissue causes orthosympathetic reflex discharges which are followed by a spontaneous post-excitation of the orthosympathetic reflex activity.

What I claim is:

1. A nerve stimulator apparatus which includes a waveform generator for generating a waveform comprising a sequence of pulses which are operatively fed to a first output terminal and a second output terminal of the apparatus, the waveform generator comprising:

current regulating means connected to the first output terminal and operable to regulate an output current of the waveform generator;

a voltage source connected to the second output terminal so that a load connectable to the first and second output terminals provides a series connection between the current regulating means and the voltage source; and a passive component connected across the first and the second output terminals to provide an exponential decay of each pulse; and a controller connected to the current regulating means and to the voltage source, said controller being operable to control the current regulating means and the voltage source so that the pulses generated by the waveform generator have a repetition rate of 150 to 200 Hz, a pulse width of 0,8 to 1,2 ms, an amplitude of between 40 and 60 Volts, and an average output current of 0,01 to 10 mA.

2. An apparatus as claimed in claim 1, in which the voltage source has voltage off-set means operable to adjust a negative DC off-set of the waveform so that each pulse has a positive peak of 10 to 600 mV and whereafter said pulse decays exponentially from a positive value to a negative value.

3. An apparatus as claimed in claim 1, in which the controller includes a microprocessor having software for controlling the waveform generator, and a frequency to voltage converter connected to the microprocessor and operable to convert a frequency dependent signal, which is sourced from the microprocessor and representative of a desired output current, to a voltage dependent signal which is fed into the current regulating means thereby to control the output current of the apparatus.

4. An apparatus as claimed in claim 1, in which the current regulating means comprises a constant current source.

5. An apparatus as claimed in claim 1, in which the voltage source comprises a constant voltage source.

6. An apparatus as claimed in claim 1, wherein said passive component comprises a capacitor.

7. A method of controlling pain in a human subject, which includes generating a waveform comprising a sequence of pulses having a repetition rate of 150 to 200 Hz, a pulse width of 0.8 to 1.2 ms, an average output current of 0.1 to 10 Ma, and applying the waveform to the human subject at an amplitude of between 40 and 60 volts, maintaining the pulse temporarily constant at said amplitude and feeding the pulse via a passive component so that the waveform thereafter decays exponentially from the temporary constant amplitude through zero volts to a negative value and remains negative for a sufficient time period to provide a negative DC off-set to the waveform.

* * * * *